United States Patent
Berezkin et al.

(10) Patent No.: US 8,114,938 B2
(45) Date of Patent: *Feb. 14, 2012

(54) POLYURETHANE DISPERSIONS FOR USE IN PERSONAL CARE PRODUCTS

(75) Inventors: Yuliya Berezkin, Pittsburgh, PA (US); Peter D. Schmitt, Beaver, PA (US); Serkan Unal, Pittsburgh, PA (US)

(73) Assignee: Bayer MaterialScience LLC, Pittsburgh, PA (US)

( * ) Notice: Subject to any disclaimer, the term of this patent is extended or adjusted under 35 U.S.C. 154(b) by 131 days.

This patent is subject to a terminal disclaimer.

(21) Appl. No.: 12/238,524

(22) Filed: Sep. 26, 2008

(65) Prior Publication Data
US 2009/0022678 A1    Jan. 22, 2009

Related U.S. Application Data

(63) Continuation of application No. 11/717,864, filed on Mar. 14, 2007, now Pat. No. 7,445,770.

(51) Int. Cl.
| | |
|---|---|
| C08G 18/08 | (2006.01) |
| C08J 3/00 | (2006.01) |
| C08K 3/20 | (2006.01) |
| C08L 75/00 | (2006.01) |
| A61K 8/04 | (2006.01) |
| A61K 8/18 | (2006.01) |
| A61K 8/72 | (2006.01) |
| A61Q 5/06 | (2006.01) |

(52) U.S. Cl. ....... 524/591; 524/839; 524/840; 424/70.1; 424/70.11; 424/70.17

(58) Field of Classification Search .............. 524/591, 524/839, 840; 424/70.1, 70.11, 70.17
See application file for complete search history.

(56) References Cited

U.S. PATENT DOCUMENTS

| | | |
|---|---|---|
| 5,626,840 A | 5/1997 | Thomaides et al. |
| 5,643,581 A | 7/1997 | Mougin et al. |
| 5,968,494 A | 10/1999 | Kukkala et al. |
| 6,007,793 A | 12/1999 | Bhatt et al. |
| 6,106,813 A | 8/2000 | Mondet et al. |
| 6,277,386 B1 | 8/2001 | Kim et al. |
| 6,291,580 B1 | 9/2001 | Kukkala et al. |
| 6,368,583 B1 | 4/2002 | Kim et al. |
| 6,407,158 B1 | 6/2002 | Kim et al. |
| 6,517,821 B1 | 2/2003 | Rollat et al. |
| 6,524,564 B1 | 2/2003 | Kim et al. |
| 6,613,314 B1 * | 9/2003 | Rollat et al. ............... 424/70.1 |
| 6,692,729 B1 | 2/2004 | Asaoka et al. |
| 6,897,281 B2 * | 5/2005 | Lubnin et al. ............... 528/44 |
| 7,452,525 B1 * | 11/2008 | Berezkin et al. ........... 424/59 |
| 2003/0044364 A1 | 3/2003 | Meyer et al. |
| 2004/0197293 A1 | 10/2004 | Mougin |
| 2007/0167565 A1 | 7/2007 | Rische et al. |
| 2007/0219296 A1 | 9/2007 | Trinks et al. |

FOREIGN PATENT DOCUMENTS

| | | | |
|---|---|---|---|
| WO | WO 2005/100427 | * | 10/2005 |

* cited by examiner

*Primary Examiner* — Patrick Niland
(74) *Attorney, Agent, or Firm* — Robert S. Klemz; Noland J. Cheung

(57) ABSTRACT

The invention relates to an aqueous polyurethane dispersion suitable for use in personal care products, the dispersed polyurethane comprising the reaction products of:

A) a prepolymer according to the formula:

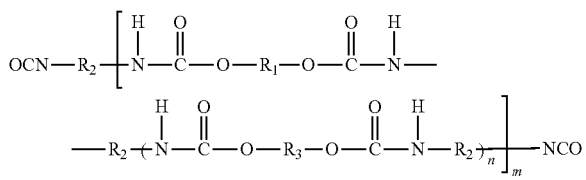

wherein
$R_1$ represents a bivalent radical of a dihydroxyl functional compound,
$R_2$ represents a hydrocarbon radical of an aliphatic or cycloaliphatic polyisocyanate,
$R_3$ represents a radical of a low molecular weight diol, optionally substituted with ionic groups,
$n$ is from 0 to 5, and
$m$ is $>1$;

B) at least one chain extender according to the formula:

$$H_2N-R_4-NH_2$$

wherein $R_4$ represents an alkylene or alkylene oxide radical not substituted with ionic or potentially ionic groups; and C) at least one chain extender according to the formula:

$$H_2N-R_5-NH_2$$

wherein $R_5$ represents an alkylene radical substituted with ionic or potentially ionic groups.

10 Claims, No Drawings

POLYURETHANE DISPERSIONS FOR USE IN PERSONAL CARE PRODUCTS

This application is a Continuation of Ser. Number 11/717,864, filed Mar. 14, 2007, now U.S. Pat. No. 7,445,770.

BACKGROUND OF THE INVENTION

The invention relates to aqueous polyurethane dispersions, to a process for preparing them and to their use in cosmetic applications such as hair fixatives.

Polyurethane dispersions have recently been incorporated into cosmetic products, such as hair fixatives, suntan lotions, etc., offering several advantages over conventional technologies such as acrylics and acryl amide copolymers, polyvinyl pyrrolidone, and PVP/VA copolymers. Such advantages include water compatibility, ease of formulating low VOC sprays, water resistance and excellent film forming ability. Specifically in hair care products, polyurethane dispersions provide great setting effect without sticky feel, excellent style retention owing to the polymer's elastic memory, natural look and feel. All these attributes are highly valuable to the consumer. Commercial polyurethane dispersions designed as hair fixatives and hair styling polymers generally exhibit good high humidity curl retention, style retention, good feel and shine. However, their lack of adhesion to hair is demonstrated by extensive flakiness on hair after combing. This creates a significant aesthetic problem for consumers.

The challenge of designing a hair fixative polymer consists of achieving a balance between often conflicting requirements: the polymer should be hydrophobic enough to provide curl retention even under humid conditions, while it should remain sufficiently hydrophilic in order to be removable from hair by washing with water. Also, the polymer has to posses an optimum combination of glass transition temperature, flexibility and molecular weight to provide setting strength, elasticity, adhesion to hair and soft feel.

U.S. Pat. No. 5,626,840 discloses hair fixatives based on polyurethane dispersions that are prepared utilizing 2,2-hydroxymethyl-substituted carboxylic acid. It illustrates how to achieve good humidity resistance and spray characteristics using water soluble or dispersable polyurethanes. The examples demonstrate the efficacy of the polymer only in aerosol spray formulations containing alcohol. This is detrimental for both the environment and the health of the hair. Finally, the invention utilizes a range of dimethylol propionic acid (DMPA) of 0.35-2.25 meq of COOH per gram of polyurethane in the polyurethane dispersion that must be observed in order for the dispersion to be effective.

However, the disclosure does not teach how to avoid the common problem of the polymer's flakiness on hair by achieving good adhesion to hair. Moreover, it does not teach how to attain style retention, e.g. elastic behavior of the polymer. Finally, a lower amount of acid should preferably be used, while still achieving curl retention and washability, as the acid tends to accelerate the breakdown of the polymer.

U.S. Pat. No. 6,613,314 discloses reshapeable hair compositions that utilize polyurethane dispersions. During preparation of the polyurethane, an isocyanate-functional prepolymer is formed. The prepolymer incorporates at least one polyactive hydrogen compound that is soluble in the medium of dispersion. Preferably, sulfonated compounds are utilized. The sulfonic group is incorporated into the prepolymer, rather than via the urea segment.

U.S. Pat. No. 6,106,813 discloses polyester polyurethanes that are suitable in cosmetic applications. It discloses a new family of polyester polyurethanes that possess not only good film-forming properties, but also impart great rigidity and excellent resistance to removal by water and detergents. With regard to the hair styling/hair fixative applications, the examples in the patent demonstrate the use of the invention only in hair style shaping lotions, claiming good shape retention.

However, the reference does not mention adhesion to hair or how to achieve excellent humidity resistance with good removability by water. It also does not mention important attributes of hair styling/hair fixative polymers, such as natural feel and luster on hair.

Thus, the purpose of present invention was to provide a polymer composition which would improve adhesion to hair and also demonstrate excellent curl and style retention, natural feel and look.

The present invention provides a composition that demonstrates excellent adhesion to hair. In comparison to commercially available hair fixative polyurethane dispersions, the composition of the present invention impart significantly less or no flaking at all. In addition, it provides improved humidity retention, higher luster and natural feel in comparison to the above-mentioned polyurethane dispersions.

SUMMARY OF THE INVENTION

The present invention relates to an aqueous polyurethane dispersion suitable for use in personal care products, the dispersed polyurethane comprising the reaction products of:

A) a prepolymer according to the formula:

$$OCN-R_2 {\left[ N(H)-C(=O)-O-R_1-O-C(=O)-N(H)-R_2 {\left( N(H)-C(=O)-O-R_3-O-C(=O)-N(H)-R_2 \right)}_n \right]}_m NCO$$

wherein
  $R_1$ represents a bivalent radical of a dihydroxyl functional compound,
  $R_2$ represents a hydrocarbon radical of an aliphatic or cycloaliphatic polyisocyanate,
  $R_3$ represents a radical of a low molecular weight diol, optionally substituted with ionic groups,
  n is from 0 to 5, and
  m is >1;

B) at least one chain extender according to the formula:

$$H_2N-R_4-NH_2$$

wherein $R_4$ represents an alkylene or alkylene oxide radical not substituted with ionic or potentially ionic groups; and C) at least one chain extender according to the formula:

$$H_2N-R_5-NH_2$$

wherein $R_5$ represents an alkylene radical substituted with ionic or potentially ionic groups.

The present invention also relates to a process for preparing a hair fixative comprising:

A) preparing an aqueous polyurethane dispersion by
   1) forming a isocyanate-functional prepolymer by reacting
      1a) a polyol,
      1b) an aliphatic or cycloaliphatic polyisocyanate, and
      1c) a low molecular weight diol optionally substituted with ionic groups;
   2) chain-extending the prepolymer with
      2a) at least one chain extender according to the formula:

$H_2N-R_4-NH_2$ wherein $R_4$ represents an alkylene or alkylene oxide radical not substituted with ionic or potentially ionic groups, and
      2b) at least one chain extender according to the formula:

$H_2N-R_5-NH_2$ wherein $R_5$ represents an alkylene radical substituted with ionic or potentially ionic groups,
      in the presence of an organic solvent to form a polyurethane;
   3) dispersing the polyurethane in water; and
   4) removing the organic solvent, resulting in an aqueous polyurethane dispersion; and
mixing the polyurethane dispersion with water or ethanol.

DETAILED DESCRIPTION OF THE PREFERRED EMBODIMENTS

Suitable dihydroxyl compounds for providing the bivalent radical $R_1$ are those having two hydroxy groups and having number average molecular weights of from about 700 to about 16,000, and preferably from about 750 to about 5000. Examples of the high molecular weight compounds are polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. The polyester polyols, polyether polyols and polyhydroxy polycarbonates are preferred. Mixtures of various such compounds are also within the scope of the present invention.

The polyester diol(s) may be prepared in known manner from aliphatic, cycloaliphatic or aromatic dicarboxylic or polycarboxylic acids or anhydrides thereof (for example, succinic, glutaric, adipic, pimelic, suberic, azelaic, sebacic, nonanedicarboxylic, decanedicarboxylic, terephthalic, isophthalic, o-phthalic, tetrahydrophthalic, hexahydrophthalic or trimellitic acid) as well as acid anhydrides (such as o-phthalic, trimellitic or succinic acid anhydride or a mixture thereof) and dihydric alcohols such as, for example, ethanediol, diethylene, triethylene, tetraethylene glycol, 1,2-propanediol, dipropylene, tripropylene, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, 1,8-octanediol, 1,10-decanediol, 1,12-dodecanediol or mixtures thereof. Cycloaliphatic and/or aromatic dihydroxyl compounds are, of course, also suitable as the dihydric alcohol(s) for the preparation of the polyester polyol(s). The corresponding polycarboxylic acid anhydrides or corresponding polycarboxylic acid esters of low alcohols, or mixtures thereof, may also be used in place of the free polycarboxylic acid for the preparation of the polyesters.

The polyester diols may naturally also be homopolymers or copolymers of lactones, which are preferably obtained by addition reactions of lactones or lactone mixtures, such as butyrolactone, ϵ-caprolactone and/or methyl-ϵ-caprolactone with the suitable difunctional starter molecules such as, for example, the low molecular weight dilyhydric alcohols mentioned above. The corresponding polymers of ϵ-caprolactone are preferred.

Polycarbonates containing hydroxy groups include those known per se such as the products obtained from the reaction of diols such as propanediol-(1,3), butanediol-(1,4) and/or hexanediol-(1,6), diethylene glycol, triethylene glycol or tetraethylene glycol with diarylcarbonates, e.g. diphenylcarbonate or phosgene.

Suitable polyether polyols are obtained in known manner by the reaction of starting compounds which contain reactive hydrogen atoms with alkylene oxides such as ethylene oxide; propylene oxide; butylene oxide; styrene oxide; tetrahydrofuran or epichlorohydrin or with mixtures of these alkylene oxides. It is preferred that the polyethers do not contain more than about 10% by weight of ethylene oxide units. Most preferably, polyethers obtained without the addition of ethylene oxide are used.

Suitable starting compounds containing reactive hydrogen atoms include, e.g. water and the dihydric alcohols set forth for preparing the polyester polyols.

Polyethers modified by vinyl polymers are also suitable according to the invention. Products of this kind may be obtained by polymerizing, e.g. styrene and acrylonitrile in the presence of polyethers (U.S. Pat. Nos. 3,383,351; 3,304,273; 3,523,095; 3,110,695 and German Pat. No. 1,152,536).

Among the polythioethers which should be particularly mentioned are the condensation products obtained from thiodiglycol on its own and/or with other glycols, dicarboxylic acids, formaldehyde, aminocarboxylic acids or amino alcohols. The products obtained are either polythio-mixed ethers, polythioether esters or polythioether ester amides, depending on the co-components.

Suitable polyacetals include the compounds which can be prepared from aldehydes, e.g. formaldehyde, and glycols such as diethylene glycol, triethylene glycol, ethoxylated 4,4'-dihydroxy-diphenyldimethylmethane, and hexanediol-(1,6). Polyacetals suitable for the purpose of the invention may also be prepared by the polymerization of cyclic acetals.

Suitable polyhydroxy polyester amides and polyamines are, for example, the predominantly linear condensates obtained from polybasic saturated and unsaturated carboxylic acids or their anhydrides and polyvalent saturated or unsaturated aminoalcohols, diamines, polyamines and mixtures thereof.

Suitable monomers for producing hydroxyfunctional polyacrylates include acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate and 2-isocyanatoethyl methacrylate.

Suitable polyalkadienes include polybutadienes and polyisoprenes, such as POLY bd resin from Elf Atochem North America, Philadelphia, Pa. Also included are hydrogenated polyisoprene and hydrogenated polybutadiene. Examples of those include KRATON L-2203 from Shell chemical, Houston, Tex., and POLYTAIL resins from Mitsubishi Chemical, Tokyo, Japan.

Mixtures of the above-described dihydroxy compounds can also be used.

Suitable polyisocyanates for providing the hydrocarbon radical $R_2$ include organic diisocyanates having a molecular weight of from about 112 to 1,000, and preferably from about 140 to 400. Preferred diisocyanates are those represented by the general formula $R_2(NCO)_2$ indicated above in which $R_2$ represents a divalent aliphatic hydrocarbon group having from 4 to 18 carbon atoms, a divalent cycloaliphatic hydrocarbon group having from 5 to 15 carbon atoms, a divalent araliphatic hydrocarbon group having from 7 to 15 carbon atoms or a divalent aromatic hydrocarbon group having 6-15 carbon atoms. Examples of the organic diisocyanates which are suitable include tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, isomers of toluene diisocyanate (TDI) such as 2,4-diisocyanatotoluene, 2,6-diisocyanatotoluene, mixtures of these isomers, hydrogenated TDI, 4,4'-diisocyanato diphenyl methane and its isomeric mixtures with 2,4'- and optionally 2,2'-diisocyanato diphenylmethane, and 1,5-diisocyanato naphthalene. Mixtures of diisocyanates can, of course, be used. Preferred diisocyanates are aliphatic and cycloaliphatic diisocyanates. Particularly preferred are 1,6-hexamethylene diisocyanate and isophorone diisocyanate.

The low molecular weight diols usually result in a stiffening of the polymer chain, and are optionally used. By "low molecular weight diols" it is meant diols having a molecular weight from about 62 to 700, preferably 62 to 200. They may contain aliphatic, alicyclic or aromatic groups. Preferred compounds contain only aliphatic groups. The low molecular weight diols having up to about 20 carbon atoms per molecule include ethylene glycol, diethylene glycol, propane 1,2-diol, propane 1,3-diol, butane 1,4-diol, butylene 1,3-glycol, neopentyl glycol, butyl ethyl propane diol, cyclohexane diol, 1,4-cyclohexane dimethanol, hexane 1,6-diol, bisphenol A (2,2-bis(4-hydroxyphenyl)propane), hydrogenated bisphenol A (2,2-bis(4-hydroxycyclohexyl)propane), and mixtures thereof.

Optionally, the low molecular weight diols may contain ionic or potentially ionic groups. Suitable lower molecular weight diols containing ionic or potentially ionic groups are those disclosed in U.S. Pat. No. 3,412,054. Preferred compounds include dimethylol butanoic acid (DMBA), dimethylol propionic acid (DMBA) and carboxyl-containing caprolactone polyester diol. If lower molecular weight diols containing ionic or potentially ionic groups are used, they are used in an amount such that <0.30 meq of COOH per gram of polyurethane in the polyurethane dispersion are present. Preferably, the low molecular weight diols containing ionic or potentially ionic groups are not used.

The prepolymer is chain extended using two classes of chain extenders. First, compounds having the formula:

$$H_2N-R_4-NH_2$$

wherein $R_4$ represents an alkylene or alkylene oxide radical not substituted with ionic or potentially ionic groups. Alkylene diamines include hydrazine, ethylenediamine, propylenediamine, 1,4-butylenediamine and piperazine. The alkylene oxide diamines include 3-{2-[2-(3-aminopropoxy)ethoxy]ethoxy}propylamine (also known as dipropylamine diethyleneglycol or DPA-DEG available from Tomah Products, Milton, Wis.), 2-methyl-1,5-pentanediamine (Dytec A from DuPont), hexane diamine, isophorone diamine, and 4,4-methylenedi-(cyclohexylamine), and the DPA-series ether amines available from Tomah Products, Milton, Wis., including dipropylamine propyleneglycol, dipropylamine dipropyleneglycol, dipropylamine tripropyleneglycol, dipropylamine poly(propylene glycol), dipropylamine ethyleneglycol, dipropylamine poly(ethylene glycol), dipropylamine 1,3-propane diol, dipropylamine 2-methyl-1,3-propane diol, dipropylamine 1,4-butane diol, dipropylamine 1,3-butane diol, dipropylamine 1,6-hexane diol and dipropylamine cyclohexane-1,4-dimethanol. Mixtures of the listed diamines may also be used.

The second class of chain extenders are compounds having the formula:

$$H_2N-R_5-NH_2$$

wherein $R_5$ represents an alkylene radical substituted with ionic or potentially ionic groups. Such compounds have an ionic or potentially ionic group and two groups that are reactive with isocyanate groups. Such compounds contain two isocyanate-reactive groups and an ionic group or group capable of forming an ionic group. The ionic group or potentially ionic group can be selected from the group consisting of ternary or quaternary ammonium groups, groups convertible into such a group, a carboxyl group, a carboxylate group, a sulfonic acid group and a sulfonate group. The at least partial conversion of the groups convertible into salt groups of the type mentioned may take place before or during the mixing with water. Specific compounds include diaminosulfonates, such as for example the sodium salt of N-(2-aminoethyl)-2-aminoethane sulfonic acid (AAS) or the sodium salt of N-(2-aminoethyl)-2-aminopropionic acid.

The polyurethane according to the invention may also include compounds which are situated in each case at the chain ends and terminate said chains (chain terminators). These chain terminators can be derived from compounds having the formula:

wherein $R_6$ is an H atom or alkylene radical optionally having a hydroxyl end and $R_7$ is alkylene radical optionally having a hydroxyl end. Suitable compounds include compounds such as monoamines, particularly monosecondary amines, or monoalcohols. Examples include: methylamine, ethylamine, propylamine, butylamine, octylamine, laurylamine, stearylamine, isononyloxy-propylamine, dimethylamine, diethylamine, dipropylamine, dibutylamine, N-methylaminopropylamine, diethyl(methyl)aminopropylamine, morpholine, piperidine, diethanolamine and suitable substituted derivatives thereof, amide amines of diprimary amines and monocarboxylic acids, monoketimes of diprimary amines, primary/tertiary amines such as N,N-dimethylaminopropylamine and the like. Also suitable are chain terminating alcohols such as, $C_1$-$C_{10}$ or higher alcohols including, methanol, butanol, hexanol, 2-ethylhexyl alcohol, isodecyl alcohol, and the like and even mixtures thereof, as well as aminoalcohols such as aminomethylpropanol (AMP).

In one embodiment of the invention, diethylene glycol is incorporated into the polyurethane dispersion either as the low molecular weight diol, or as part of the non-ionic chain extender through the use of dipropylamine-diethyleneglycol. If the diethylene glycol is used as the low molecular weight diol, then preferably the DPA-DEG is not used as the non-ionic chain extender. Likewise, if the DPA-DEG is used as the non-ionic chain extender, then diethylene glycol is preferably not used as the low molecular weight diol. The use of the diethylene glycol or DPA-DEG is especially desirable when the polyurethane dispersion is incorporated into a hair fixative, as the diethylene glycol significantly increases the adhesion to hair.

The present invention also relates to a process for the production of a polyurethane dispersion suitable for use in personal care products, comprising a) reacting in a first step at least the dihydroxyl compounds and the diisocyanate to form the prepolymer A), then b) dissolving in a second step the prepolymer in an organic solvent and c) reacting in a third step the isocyanate-containing prepolymer solution with the two classes of chain extenders and optionally, the chain terminator, d) forming, in a fourth step, the dispersion by addition of water, and e) removing in a fifth step the organic solvent.

Free sulfonic acid groups incorporated are neutralized between the third and fourth step. Suitable neutralizing agents include are the primary, secondary or tertiary amines. Of these the trialkyl-substituted tertiary amines are preferred. Examples of these amines are trimethyl amine, triethyl amine, triisopropyl amine, tributyl amine, N,N-dimethyl-cyclohexyl amine, N,N-dimethylstearyl amine, N,N-dimethylaniline, N-methylmorpholine, N-ethylmorpholine, N-methylpiperazine, N-methylpyrrolidine, N-methylpiperidine, N,N-dimethyl-ethanol amine, N,N-diethyl-ethanol amine, triethanolamine, N-methyldiethanol amine, dimethylaminopropanol, 2-methoxyethyldimethyl amine, N-hydroxyethylpiperazine, 2-(2-dimethylaminoethoxy)-ethanol and 5-diethylamino-2-pentanone. The most preferred tertiary amines are those which do not contain active hydrogen(s) as determined by the Zerewitinoff test since they are capable of reacting with the isocyanate groups of the prepolymers which can cause gelation, the formation of insoluble particles or chain termination.

The polyurethane dispersions according to the invention can be produced by the so-called acetone process. In the acetone process the synthesis of the aqueous preparations of polyurethane on which the dispersions according to the invention are based is performed in a multistage process.

In a first stage a prepolymer containing isocyanate groups is synthesized from the dihydroxyl compound, the diisocyanate and the low molecular weight diol. The amounts of the individual components are calculated in such a way that the isocyanate content of the prepolymers is between 1.4 and 5.0 wt. %, preferably between 2.0 and 4.5 wt. %, and particularly preferably between 2.6 and 4.0 wt. %. The low molecular weight diol is present in an amount from 0 to 80 eq. % based on the amount of NCO equivalents, preferably from 0 to 10 eq. %.

The resulting prepolymer has a structure of:

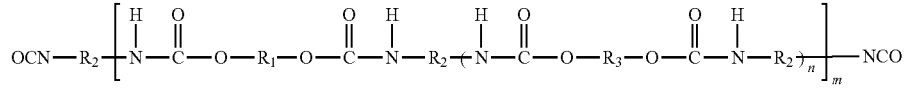

wherein
$R_1$ represents a bivalent radical of a dihydroxyl functional compound,
$R_2$ represents a hydrocarbon radical of an aliphatic or cycloaliphatic polyisocyanate,
$R_3$ represents a radical of a low molecular weight diol, optionally substituted with ionic groups,
n is <5, and
m is >1.
Preferably, n is from 1 to 3, and m is from 1 to 5.

In a second stage the prepolymer produced in stage 1 is dissolved in an organic, at least partially water-miscible, solvent containing no isocyanate-reactive groups. The preferred solvent is acetone. Other solvents, such as, for example, 2-butanone, tetrahydrofuran or dioxan or mixtures of these solvents can also be used, however. The quantities of solvent to be used must be calculated in such a way that a solids content of 25 to 60 wt. %, preferably 30 to 50 wt. %, particularly preferably 35 to 45 wt. %, is obtained.

In a third stage the isocyanate-containing prepolymer solution is reacted with mixtures of the amino-functional chain extenders and, optionally, chain terminator, to form the high-molecular weight polyurethane. Sufficient amounts of the chain extenders and chain terminator are used such that the calculated number-average molecular weight (Mn) of the resulting polyurethane is between 10,000 and 100,000 daltons, preferably between 10,000 and 50,000 daltons. The non-ionic chain extender is present in an amount from 15 to 90 eq. %, preferably 35.0 to 55 eq. %, based on the residual amount of NCO equivalents present in the prepolymer. The ionic chain extender is present in an amount from 10 to 50 eq. %, preferably from 25 to 35 eq. %, based on the residual amount of NCO equivalents present in the prepolymer. The chain terminator is present in an amount from 0 to 35 eq. %, preferably from 20 to 30 eq. %, based on the residual amount of NCO equivalents present in the prepolymer.

In a fourth stage the high-molecular weight polyurethane is dispersed in the form of a fine-particle dispersion by addition of water to the solution or solution to the water.

In a fifth stage the organic solvent is partially or wholly removed by distillation, optionally under reduced pressure. The amount of water in stage four is calculated in such a way that the aqueous polyurethane dispersions according to the invention display a solids content of 20 to 60 wt. %, preferably 28 to 42 wt. %.

The polyurethane dispersions of the present invention are suitable for use in personal care products. Preferably, they are used in non-aerosol hair fixatives. Such hair fixatives are easily prepared by the addition of water or ethanol to the dispersion. Likewise, the dispersions may be used in the preparation of other personal care products such as suntan lotions, skin care products, lipstick, mascara and deodorants, by the addition of components well known to those of ordinary skill in the art.

EXAMPLES

Non-aerosol hair fixative formulations were prepared utilizing deionized water and the polyurethane dispersions according to the invention. The formulations were 4 parts polyurethane dispersion active resin solids by the mixing of 10 parts polyurethane dispersion and 90 parts water. The non-aerosol spray formulations (20 ml) containing 3% active resin solids were prepared as following: ((3/% solids PUD)×20 ml)/100=X g of PUD dissolved in (20−X) g of water.

Products Used in the Examples:

Desmophen® PE-170HN: polyesterdiol (M/wt. 1700, OH No. 66; adipic acid hexanediol neopentyl glycol ester, Bayer MaterialScience LLC, Pittsburgh, Pa.)

Desmodur® H (1,6-hexamethylene diisocyanate, Bayer MaterialScience LLC, Pittsburgh, Pa.)

DPA-DEG (dipropylamine-diethyleneglycol, Tomah Products, Milton, Wis.)

Kathon® LX (biocide, Rohm & Haas, Philadelphia, Pa.)

Microcare® MTG (biocide, Thor Specialties (UK) Ltd., Cheshire, UK)

Example 1

Composition According to the Invention 32.08 g of Desmophen® PE-170HN, polyesterdiol (M/wt. 1700, OH No. 66; adipic acid hexanediol neopentyl glycol ester) and 0.19 g of neopentyl glycol were reacted with 5.71 g of Desmodur® H (1,6-hexamethylene diisocyanate). When the reaction reached theoretical NCO %, the resulting prepolymer was cooled to 60° C. and dissolved in 60 g of acetone. After mixing for 30 minutes, a solution of 0.66 g of dipropylamine-diethyleneglycol (DPA-DEG from Tomah Products), 1.70 g of AAS (N-(2-aminoethyl)-2-aminoethane sulfonic acid) sodium salt, 0.16 g of ethylenediamine and 0.61 g of diethanolamine (DEOA) in 8.53 g distilled water was added dropwise. After mixing for 20 minutes, 58.14 g of distilled water at room temperature were added into reactor and the acetone was subsequently distilled off under reduced pressure. 0.52 g of biocide, Kathon® LX was added into the final product under agitation.

Example 2

Composition According to the Invention 31.95 g of Desmophen® PE-170HN, polyesterdiol (M/wt. 1700, OH No. 66; adipic acid hexanediol neopentyl glycol ester) and 0.24 g of dimethylol butanoic acid (DMBA) were reacted with 5.69 g of Desmodur® H (1,6-hexamethylene diisocyanate). When the reaction reached theoretical NCO %, the resulting prepolymer was cooled to 60° C. and dissolved in 60 g of acetone. After mixing for 20 minutes, 0.17 g of AMP-95 (95% aq. solution of 2-amino-2-methyl-1-propanol) was added to the mixture to neutralize the acid. A solution of 1.31 g of dipropylamine-diethyleneglycol (DPA-DEG from Tomah Products), 1.05 g of AAS sodium (N-(2-aminoethyl)-2-aminoethane sulfonic acid) salt and 0.93 g of diethanolamine (DEOA) in 8.53 g distilled water was added dropwise. After mixing for 20 minutes, 58.14 g of distilled water at room temperature were added into reactor and the acetone was subsequently distilled off under reduced pressure. 0.52 g of biocide, Microcare® MTG was added into the final product under agitation.

Example 3

Comparative Example 32.22 g of Desmophen® PE-170HN, polyesterdiol (M/wt. 1700, OH No. 66; adipic acid hexanediol neopentyl glycol ester) were reacted with 5.74 g of Desmodur® H (1,6-hexamethylene diisocyanate). When the reaction reached theoretical NCO %, the resulting prepolymer was cooled to 60° C. and dissolved in 60 g of acetone. After mixing for 30 minutes, a solution of 1.52 g of AAS (N-(2-aminoethyl)-2-aminoethane sulfonic acid) sodium salt and 0.33 g of ethylenediamine in 8.53 g distilled water was added dropwise. After mixing for 20 minutes, 60.22 g of distilled water at room temperature were added into reactor and the acetone was subsequently distilled off reduced pressure. 0.52 g of biocide, Kathon® LX was added into the final product.

Example 4

Composition According to the Invention 30.70 g of Desmophen® PE-170HN, polyesterdiol (M/wt. 1700, OH No. 66; adipic acid hexanediol neopentyl glycol ester) and 0.23 g of neopentyl glycol were reacted with 5.45 g of Desmodur® H(1,6-hexamethylene diisocyanate). When the reaction reached theoretical NCO %, 0.25 g of diethylene glycol was added into the reaction mixture: reaction proceeded for 1 hour at 90 C. The resulting prepolymer was cooled to 60° C. and dissolved in 60 g of acetone. After mixing for 30 minutes, a solution, 1.62 g of AAS (N-(2-aminoethyl)-2-aminoethane sulfonic acid) sodium salt, 0.11 g of ethylenediamine and 0.79 g of diethanolamine (DEOA) in 8.5 g distilled water was added dropwise. After mixing for 20 minutes, 60.36 g of distilled water at room temperature were added into reactor and the acetone was subsequently distilled off under reduced pressure. 0.5 g of biocide, Kathon LX, 1.5% solids solution, was added into the final product under agitation.

Curl retention testing was performed in accordance with the test methods detailed in U.S. Pat. No. 5,626,840. Spray bottles with fine mist were used for application. The sample hair used was Yaki brown hair, 8 in., color 4. The Curl Retention test was performed as follows. The hair is cut into swatches of ~2 g. each and bound together at one end. Each swatch is washed in 10% solution of clarifying shampoo for 30 seconds and rinsed in warm tap water. The hair is cut into 6 in. lengths from secured end. The hair is wet again and then combed, and the excess water is squeezed out. The hair swatches are rolled and secured onto ½ in. diameter roller and dried at 49° C. for approximately an hour. The dried hair is removed from the roller and the resulting curl is suspended by the bound end. The curl height is measured for each swatch.

Each curl is sprayed uniformly with 4 sprays per side. The curl is placed in an aluminium pan and placed in a 49° C. oven for about 30 minutes to dry. The dried curl is then resuspended, and the curl length is measured for time 0 minutes, and set into Thermotron at 22° C., 95% R.H. The curl height is measured after 24 hours.

Curl retention was calculated as follows:

$$\% \text{ Curl Retention} = \frac{L - L'}{L - L°} \times 100$$

where L is length of hair fully extended, 6 in.

L° is length of curl before spray and exposure, and

L' is length of curl after spray and exposure.

Style retention was evaluated as follows: after 24 hours exposure to high humidity, the curl was combed 10 times. The style retention was judged based on the curl's ability to retain its initial shape and length. In most cases, the curl remained unaffected by combing.

Feel was evaluated as follows: untreated hair and hair and treated with PUD were subjected to a panel of 10 judges. Panellists were asked to rank the feel from 1-5, with 1 being the most natural soft feel with no revealing presence of the polymer. Adhesion to hair was evaluated by running a comb through the treated hair, and visually observing the comb and the hair for flakes and residue.

| Component | Ex. 1 | Ex. 2 | Ex. 3 (Comp.) | Ex. 4 | Ex. 5 (Comp.) | Ex. 6 (Comp.) | Ex. 7 (Comp.) |
|---|---|---|---|---|---|---|---|
| Desmophen PE 170HN | 32.08 | 31.95 | 32.22 | 30.70 | 32.23 | 32.23 | 32.24 |
| DMBA | 0 | 0.24 | 0 | 0 | 0 | 0 | 0.17 |
| Neopentylglycol | 0.19 | 0 | 0 | 0.23 | 0 | 0.19 | 0 |
| Desmodur H | 5.71 | 5.69 | 5.71 | 5.45 | 5.74 | 5.74 | 5.74 |
| Triethylamine | 0 | 0 | 0 | 0 | 0 | 0 | 0.13 |
| AMP 95 | 0 | 0.17 | 0 | 0 | 0 | 0 | 0 |
| AAS Na salt | 1.7 | 1.05 | 1.52 | 1.62 | 1.52 | 1.73 | 1.06 |
| Dipropylamine diethyleneglycol | 0.66 | 1.31 | 0 | 0 | 0 | 0 | 0 |
| Diethanolamine | 0.61 | 0.93 | 0 | 0.79 | 1.07 | 0.62 | 1.04 |
| Ethylenediamine | 0.16 | 0 | 0.33 | 0.11 | 0.33 | 0.33 | 0.33 |
| Diethylene Glycol | 0 | 0 | 0 | .25 | 0 | 0 | 0 |
| Water | 58.37 | 58.14 | 60.22 | 60.36 | 58.6 | 58.64 | 58.77 |
| % Solids | 36.5 | 37.8 | 40.0 | 35.0 | 34.0 | 34.1 | 35.0 |
| pH | 6-8 | 7.14 | 6-8 | N/A | 7.01 | N/A | N/A |
| Mean particle size, nm | 175 | 146 | 250 | 165 | 255 | 171 | 285 |
| Viscosity @ 25 C., cps | 171 | 135 | 300 | 89 | 54 | 57 | 59 |

| Property | Ex. 1 | Ex. 2 | Ex. 3 | Ex. 4 | Ex. 5 | Ex. 6 | Ex. 7 |
|---|---|---|---|---|---|---|---|
| % Curl Retention | 95 | 92 | 97.5 | 95 | 96 | 85 | 83 |
| Style Retention | 2 | 2.5 | 1 | 1 | 1 | 2 | 1 |
| Adhesion to Hair | 1 | 1 | 5 | 1 | 2 | 3 | 3 |
| Feel | 1 | 2.5 | 2 | 2 | 2 | 1 | 2 |
| Removability | 1 | 1 | 1 | 1 | 1 | 1 | 1 |

As can be seen, Examples 1 and 2, according to the invention, gave surprisingly good results with regard to adhesion to hair, feel and removability, while still providing acceptable results with regard to curl and style retention. In contrast, in the comparative examples, white soft globular residue was observed on hair after drying and combing. The flakiness was extensive and very notable. The polymer's residue was also observed on the comb.

Example 8

Suntan Lotion

A suntan lotion was formulated using the polyurethane dispersion of Example 1, and having an SPF rating of 30+:

| Phase | Ingredients | Wt. % |
|---|---|---|
| A-water | Propylene Glycol | 1.00 |
| | D.I. water | 59.75 |
| | PUD of Example 1 | 5.00 |
| | Polargel UV 1116 (Amcol) | 3.75 |
| | Methylparaben and Butylparaben, and Propylparaben | 1.0 |
| B-Oil | Octyl methoxycinnamate | 5.0 |
| | Octyl salicylate | 3.0 |
| | Oxybenzone | 3.0 |
| | Avobenzone | 2.0 |
| | Isopropyl Myristate | 5.0 |
| | Stearyl Alcohol | 2.0 |
| | Glyceryl Stearate | 2.0 |
| | Stearic acid | 2.0 |
| | Polyethylene | 2.5 |
| | Cetyl Phosphate | 1.0 |
| Total | | 100.00 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a hair fixative comprising:
   a. preparing an aqueous polyurethane dispersion by
      i. forming a isocyanate-functional prepolymer by reacting
         1a) a polyol,
         1b) an aliphatic or cycloaliphatic polyisocyanate, and
         1c) a low molecular weight diol optionally substituted with ionic groups;
      ii. chain-extending the prepolymer with
         2a) at least one chain extender according to the formula:

$$H_2N—R_4—NH_2$$

wherein $R_4$ represents an alkylene or alkylene oxide radical not substituted with ionic potentially ionic groups, and
         2b) at least one chain extender selected from the group consisting of the sodium salt of N-(2-aminoethyl)-2-aminoethane sulfonic acid and compounds according to the formula:

$$H_2N—R_5—NH_2$$

wherein $R_5$ represents an alkylene radical substituted with ionic or potentially ionic groups,
         in the presence of an organic solvent to form a polyurethane;
      iii. dispersing the polyurethane in water; and
      iv. removing the organic solvent, resulting in an aqueous polyurethane dispersion; and
   b. mixing the polyurethane dispersion with biocide.

2. The process of claim 1, wherein the reactants further include a chain terminator according to the formula:

wherein $R_6$ is an H atom or alkylene radical optionally having a hydroxyl end and $R_7$ is alkylene radical optionally having a hydroxyl end.

3. The process of claim 2, wherein the chain terminator is selected from the group consisting of methylamine, ethylamine, propylamine, butylamine, octylamine, laurylamine, stearylamine, isononyloxy-propylamine, dimethylamine, diethylamine, dipropylamine, dibutylamine, N-methylaminopropylamine, diethyl(methyl)aminopropylamine, morpholine, piperidine and diethanolamine, amide amine of diprimary amines and monocarboxylic acids, monoketimes of diprimary amines, primary/tertiary amines, methanol, butanol, hexanol, 2-ethylhexyl alcohol, isodecyl alcohol, aminomethylpropanol and mixtures thereof.

4. The process of claim 1, wherein the polyisocyanate is selected from the group consisting of tetramethylene diisocyanate, 1,6-hexamethylene diisocyanate, dodecamethylene diisocyanate, 1,4-diisocyanatocyclohexane, 3-isocyanatomethyl-3,5,6-trimethyl-cyclohexylisocyanate (isophorone diisocyanate), 4,4'-diisocyanatodicyclo-hexylmethane, 4,4'-diisocyanatodicyclohexylpropane-(2,2) and mixtures thereof.

5. The process of claim 1, wherein the low molecular weight diol is selected from the group consisting of ethylene glycol, diethylene glycol, propane 1,2-diol, propane 1,3-diol, butane 1,4-diol, butylene 1,3, glycol, cyclohexane diol, 1,4-cyclohexane dimethanol, hexane 1,6-diol, bisphenol A (2,2-bis(4-hydroxyphenyl)propane), hydrogenated bisphenol A (2,2-bis(4-hydroxycyclohexyl)propane) and mixtures thereof.

6. The process of claim 1, wherein the first chain extender 2a) is a mixture of 3-{2-[2-(3-aminopropoxy)ethoxy]ethoxy}propylamine and ethylenediamine.

7. The process of claim 3, wherein the first chain extender 2a) is a mixture of 3-{2-[2-(3-aminopropoxy)ethoxy]ethoxy}propylamine, and ethylenediamine.

8. The process of claim 1, wherein the second chain extender 2b) is the sodium salt of N-(2-aminoethyl)-2-aminoethane sulfonic acid.

9. The process of claim 1, wherein n is from 1 to 3, and m is from 1 to 5.

10. The process of claim 1, wherein either $R_3$ is a radical diethylene glycol or $R_4$ is a radical of 3-{2-[2-(3-aminopropoxy)ethoxy]ethoxy}propylamine.

* * * * *